(12) United States Patent
Biedermann et al.

(10) Patent No.: US 9,510,868 B2
(45) Date of Patent: Dec. 6, 2016

(54) POLYAXIAL BONE ANCHORING DEVICE

(71) Applicant: BIEDERMANN TECHNOLOGIES GMBH & CO. KG, Donaueschingen (DE)

(72) Inventors: Lutz Biedermann, VS-Villingen (DE); Timo Biedermann, Trossingen (DE); Berthold Dannecker, St. Georgen (DE); Wilfried Matthis, Weisweil (DE)

(73) Assignee: Biedermann Technologies GmbH & Co. KG, Donaueschingen (DE)

( * ) Notice: Subject to any disclaimer, the term of this patent is extended or adjusted under 35 U.S.C. 154(b) by 326 days.

(21) Appl. No.: 13/907,329

(22) Filed: May 31, 2013

(65) Prior Publication Data

US 2013/0338716 A1 Dec. 19, 2013

Related U.S. Application Data

(60) Provisional application No. 61/654,593, filed on Jun. 1, 2012.

(30) Foreign Application Priority Data

Jun. 1, 2012 (EP) ..................................... 12170595

(51) Int. Cl.
*A61B 17/70* (2006.01)

(52) U.S. Cl.
CPC ....... *A61B 17/7037* (2013.01); *A61B 17/7035* (2013.01)

(58) Field of Classification Search
CPC ........................ A61B 17/7037; A61B 17/7035

(Continued)

(56) References Cited

U.S. PATENT DOCUMENTS 5,380,325 A * 1/1995 Lahille ............... A61B 17/7041
403/294
6,022,350 A 2/2000 Ganem
(Continued)

FOREIGN PATENT DOCUMENTS

CN 101810510 A 8/2010
CN 101828949 A 9/2010

OTHER PUBLICATIONS

European Search Report and Opinion for EP application No. 12170595.8 mailed by the EPO on Oct. 1, 2012 (7 pages).
(Continued)

*Primary Examiner* — Ellen C Hammond
*Assistant Examiner* — Stuart S Bray
(74) *Attorney, Agent, or Firm* — Lewis Roca Rothgerber Christie LLP

(57) ABSTRACT

A polyaxial bone anchoring device is provided comprising a bone anchoring element having a shank to be anchored in the bone and a head; a receiving part coupled to the shank and configured to pivotably receive the head, and having a channel for receiving a rod and a longitudinal axis; a pressure member arranged in the receiving part and configured to exert pressure onto the head to lock the head; a locking member that is insertable into the channel, the locking member comprising a top end and a bottom end facing the pressure member; a deformable first portion and a second portion provided at the bottom end; wherein, when the locking member is advanced into the channel along the longitudinal axis the deformable first portion is deformed resulting in a load applied to the pressure member that clamps the head, and the second portion clamps the rod.

21 Claims, 4 Drawing Sheets

(58) Field of Classification Search
USPC .................................................. 606/246–278
See application file for complete search history.

(56) References Cited

U.S. PATENT DOCUMENTS

| | | | | |
|---|---|---|---|---|
| 6,241,730 | B1* | 6/2001 | Alby .................. | A61B 17/7007 403/120 |
| RE39,089 | E * | 5/2006 | Ralph ................ | A61B 17/7032 606/278 |
| 7,658,739 | B2* | 2/2010 | Shluzas .............. | A61B 17/7023 606/250 |
| 7,744,636 | B2 | 6/2010 | Richelsoph | |
| 7,842,073 | B2 | 11/2010 | Richelsoph et al. | |
| 7,909,855 | B2 | 3/2011 | Drewry et al. | |
| 7,972,364 | B2 | 7/2011 | Biedermann et al. | |
| 8,057,523 | B2 | 11/2011 | Densford et al. | |
| 8,088,152 | B2* | 1/2012 | Schumacher ...... | A61B 17/7037 606/264 |
| 8,353,932 | B2* | 1/2013 | Jackson .............. | A61B 17/701 606/246 |
| 8,465,528 | B2 | 6/2013 | Schumacher | |
| 8,529,609 | B2* | 9/2013 | Helgerson .......... | A61B 17/7064 606/247 |
| 8,920,475 | B1* | 12/2014 | Ziemek .............. | A61B 17/7052 606/267 |
| 2003/0100904 | A1* | 5/2003 | Biedermann ...... | A61B 17/7032 606/272 |
| 2003/0125741 | A1* | 7/2003 | Biedermann ...... | A61B 17/7032 606/278 |
| 2004/0097933 | A1* | 5/2004 | Lourdel ............. | A61B 17/7037 606/266 |
| 2004/0236330 | A1 | 11/2004 | Purcell et al. | |
| 2004/0267264 | A1* | 12/2004 | Konieczynski .... | A61B 17/7032 606/289 |
| 2005/0131410 | A1* | 6/2005 | Lin .................... | A61B 17/7037 606/266 |
| 2005/0216003 | A1 | 9/2005 | Biedermann et al. | |
| 2005/0267472 | A1* | 12/2005 | Biedermann ...... | A61B 17/7037 606/308 |
| 2006/0100622 | A1* | 5/2006 | Jackson ............. | A61B 17/7037 606/304 |
| 2006/0293664 | A1* | 12/2006 | Schumacher ...... | A61B 17/7037 606/254 |
| 2007/0260246 | A1 | 11/2007 | Biedermann | |
| 2007/0286703 | A1* | 12/2007 | Doubler .................. | F16B 21/16 411/433 |
| 2008/0086131 | A1* | 4/2008 | Daly .................. | A61B 17/7032 606/264 |
| 2008/0147121 | A1* | 6/2008 | Justis ................. | A61B 17/7001 606/246 |
| 2008/0215095 | A1* | 9/2008 | Biedermann ...... | A61B 17/7031 606/246 |
| 2008/0294202 | A1* | 11/2008 | Peterson ............ | A61B 17/7032 606/305 |
| 2009/0093844 | A1 | 4/2009 | Jackson | |
| 2009/0163962 | A1 | 6/2009 | Dauster et al. | |
| 2010/0057126 | A1 | 3/2010 | Hestad | |
| 2010/0131017 | A1 | 5/2010 | Farris et al. | |
| 2010/0228293 | A1* | 9/2010 | Courtney .......... | A61B 17/7037 606/264 |
| 2011/0152947 | A1* | 6/2011 | Kirschman ........ | A61B 17/7032 606/302 |
| 2011/0270321 | A1* | 11/2011 | Prevost .............. | A61B 17/7002 606/305 |
| 2012/0035662 | A1* | 2/2012 | Vincent-Prestigiacomo ... | A61B 17/7005 606/264 |
| 2012/0277874 | A1* | 11/2012 | Yuan ....................... | A61L 27/56 623/17.16 |
| 2013/0018420 | A1 | 1/2013 | Kim | |
| 2014/0257411 | A1* | 9/2014 | Rezach ............. | A61B 17/7037 606/305 |
| 2015/0032162 | A1* | 1/2015 | Biedermann ...... | A61B 17/7032 606/278 |

OTHER PUBLICATIONS

CN Office action dated May 3, 2016 for Application No. 201310203914.3, 10 pages.

* cited by examiner

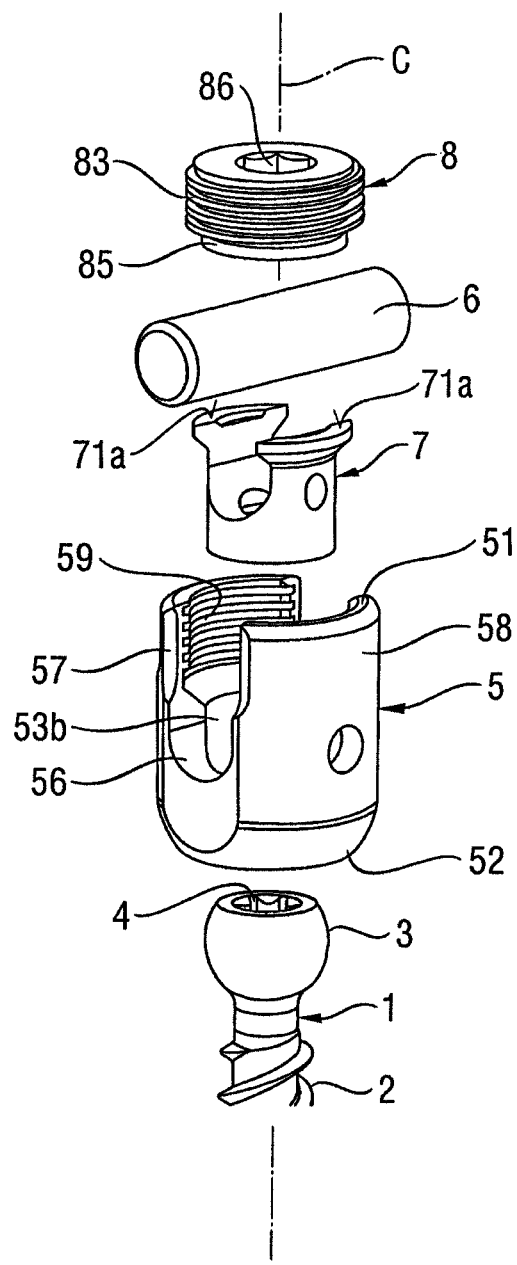
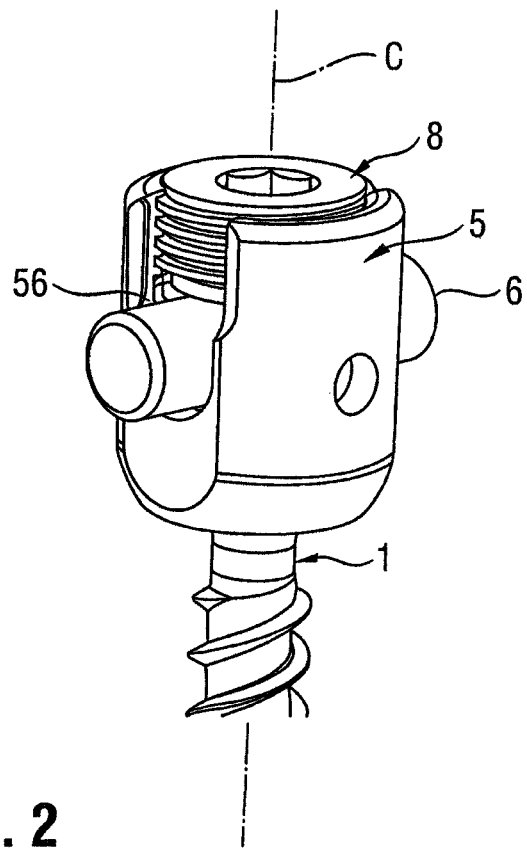
Fig. 1
Fig. 2

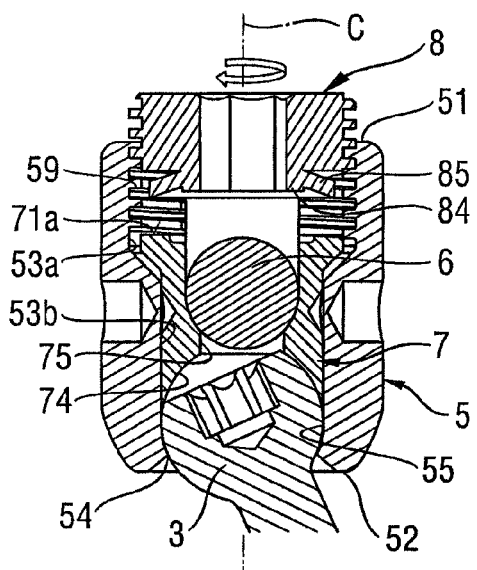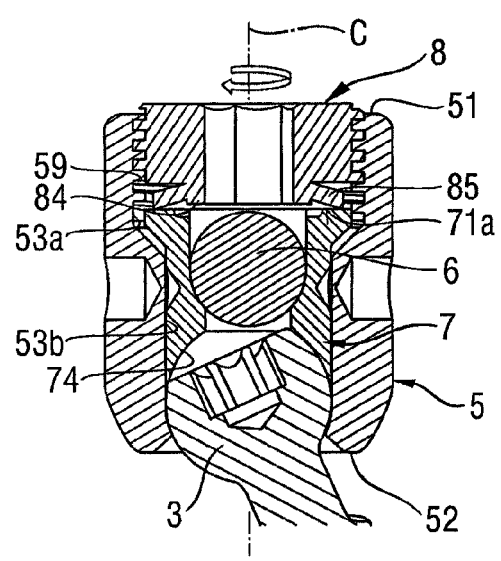
Fig. 9    Fig. 10
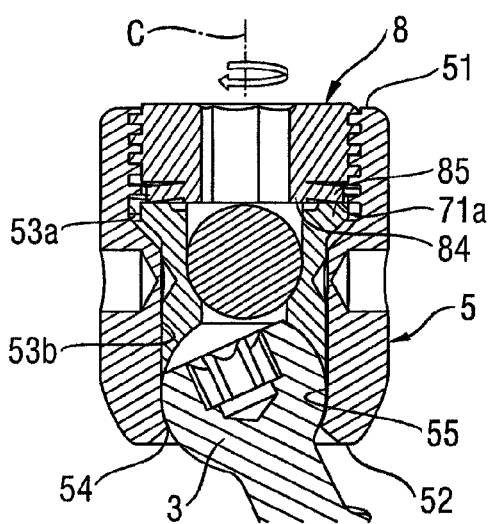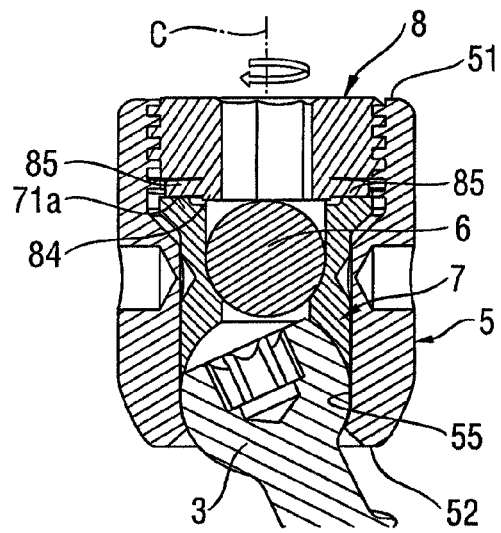
Fig. 11    Fig. 12
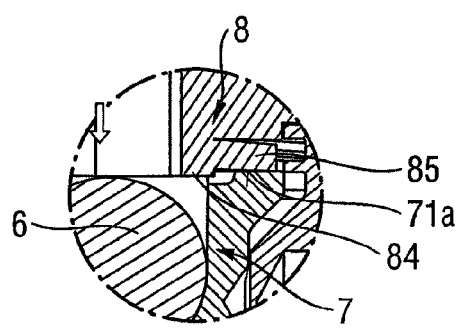
Fig. 13

POLYAXIAL BONE ANCHORING DEVICE

CROSS-REFERENCE TO RELATED APPLICATIONS

The present disclosure claims the benefit of U.S. Provisional Patent Application Ser. No. 61/654,593, filed Jun. 1, 2012, the contents of which are hereby incorporated by reference in their entirety, and claims priority from European Patent Application EP 12170595.8, filed Jun. 1, 2012, the contents of which are hereby incorporated by reference in their entirety.

BACKGROUND

1. Field of the Invention

The invention relates to a polyaxial bone anchoring device, in particular for use in spinal or trauma surgery. The polyaxial bone anchoring device comprises a bone anchoring element with a shank to be anchored in the bone and a head. The head is pivotably held in a receiving part and can be fixed at an angle by applying pressure onto it via a pressure element. With the receiving part, the bone anchoring element can be coupled to a stabilization rod that is placed into a channel of the receiving part. The polyaxial bone anchoring device further includes a locking member that is insertable into the channel and that has a deformable first portion and a second portion on its side facing the pressure member. When the locking member is advanced into the channel, first the deformable first portion comes into contact with the pressure member and is deformed resulting in a load applied to the pressure member that clamps the head, and thereafter the second portion comes into contact with the rod and clamps the rod. With such a locking member the head and the rod can be fixed in a sequential manner using a tool with a single drive portion that engages the locking member.

2. Description of Related Art

U.S. Pat. No. 7,972,364 describes a locking assembly for securing a rod in a rod receiving part of a bone anchoring device that includes a first locking element and a second locking element. With the first locking element and the second locking element the head of the bone anchoring element and the rod can be locked independently using a tool with two drive portions.

U.S. Pat. No. 8,088,152 B2 describes an orthopedic retaining system comprising at least one bone screw which has a head part and a threaded shaft pivotably mounted thereon. A clamping element is mounted in the head part, which can be pressed against the threaded shaft from its upper side and, as a result, secure the threaded shaft relative to the head part. A retaining bar is arranged in a receptacle of the head part. Further, a clamping device is provided on the upper side of the head part, by means of which the clamping element and the retaining bar are pressed into the head part such that the threaded shaft and the retaining bar are secured in positions relative to the head part. The clamping device comprises an elastically deformable pressure element which is displaced into a clamping position during actuation of the clamping device. With such a configuration, upon actuation of the clamping device, the pressure element abuts first on the clamping element and thereby secures the pivotable threaded shaft in position on the head part while the retaining bar remains freely displaceable. Only upon further actuation of the clamping device the pressure element is elastically deformed thereby abutting on the retaining bar and securing the retaining bar in position.

SUMMARY

It is the object of the invention to provide an improved polyaxial bone anchoring device that provides for a simplified handling and a reliable fixation of the head and the rod.

An embodiment of the polyaxial bone anchoring device allows the surgeon to lock both the head of the bone anchoring element in the receiving part and the rod in a sequential manner using only a single tool with a single drive portion. By this sequential locking mechanism, it is possible to first lock or at least preliminarily clamp the head and thereafter clamp the rod and finally lock the rod and the head. Moreover, a full locking of the head and the rod can be carried out and thereafter the fixation of the rod can be loosened to perform adjustments of the rod.

In an embodiment, because only a single tool with a single drive portion and one-piece locking member is needed for performing these steps, the use of the polyaxial bone anchoring device is facilitated.

In another embodiment, when the deformable portion of the locking member is elastically deformed, it is possible to perform revisions of the polyaxial anchoring device by removing the locking member and using it again.

The deformable portion may be designed as a separate part that is fixed to the locking member in order to be able to vary the clamping force by selecting an appropriate deformable portion in view of the material and the shape of the deformable portion used.

The polyaxial bone anchoring device comprises only a few parts. The locking member can be used with existing polyaxial bone anchoring devices that allow a separate head and rod fixation.

BRIEF DESCRIPTION OF THE DRAWINGS

Further features and advantages will become apparent from and will be best understood by reference to the following detailed description reviewed in conjunction with the accompanying drawings. In the drawings:

FIG. 1 shows a perspective exploded view of the polyaxial bone anchoring device according to a first embodiment.

FIG. 2 shows a perspective view of the polyaxial bone anchoring device of FIG. 1 in an assembled state.

FIGS. 9 to 12 show cross-sectional views of steps of use of the polyaxial bone anchoring device according to the first embodiment, the section taken in a plane perpendicular to the rod axis.

FIG. 13 shows an enlarged portion of a detail of FIG. 12.

DETAILED DESCRIPTION

Figure 3:
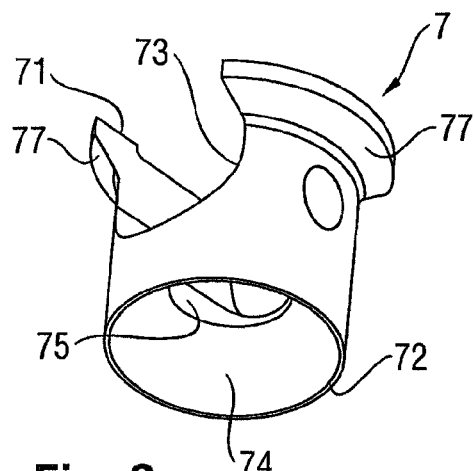
FIG. 3 shows a perspective view from the bottom of the pressure member of the polyaxial bone anchoring device according to the first embodiment.

Referring to FIGS. 1 and 2 as well as FIGS. 9 to 12, a receiving part 5 has a top end 51 and a bottom end 52 and is of substantially cylindrical construction with a longitudinal axis C extending through the top end and the bottom end. Coaxial to the longitudinal axis C, a bore 53 is provided extending from the top end 51 to a predetermined distance from the bottom end 52. The bore 53 has a first section 53a with a first diameter adjacent the top end and a second section 53b, below the first section 53a, with a second diameter smaller than the first diameter. An inclined shoulder is between the first section 53a and the second section 53b. At the bottom end 52, an opening 54 is provided, the diameter of which is smaller than the diameter of the bore 53. The coaxial bore narrows towards the opening 54, for example, with a spherically-shaped section 55 that provides a seat for a head 3 of an anchoring element. However, the section 55 can have any other shape such as, for example, a conical shape, that ensures that the head 3 is being pivotably held in the receiving part 5 similar to a ball and socket joint.

The receiving part 5 further comprises a U-shaped recess 56 starting at the top end 51 and extending in the direction of the bottom end 52. By means of the U-shaped recess 56, two free legs 57, 58 are formed that are open towards the top end 51 and define a channel for receiving the rod 6. Adjacent to the top end 51, a portion with an internal thread 59 is provided at the inner surface of the legs 57, 58. In the embodiment shown, the internal thread 59 is a flat thread having substantially horizontal upper and lower thread flanks. Any other thread form can be used for the internal thread 59; however, a thread form that reduces or eliminates splaying of the legs is preferable.

Figure 4:
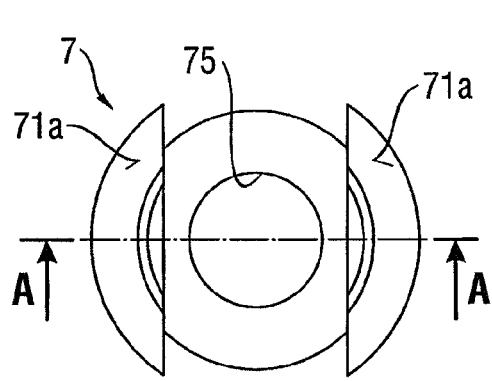
FIG. 4 shows a top view of the pressure member of FIG. 3.
Figure 5:
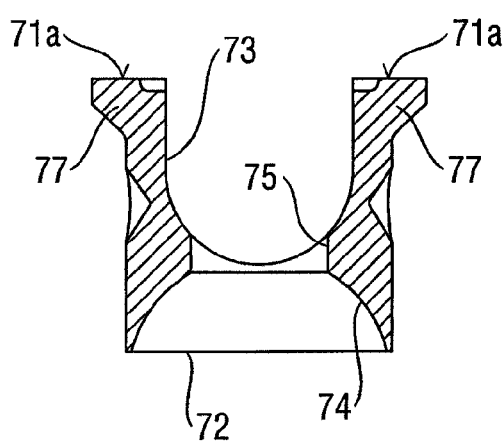
FIG. 5 shows a cross-sectional view of the pressure member along line A-A in FIG. 4.
Figure 6:
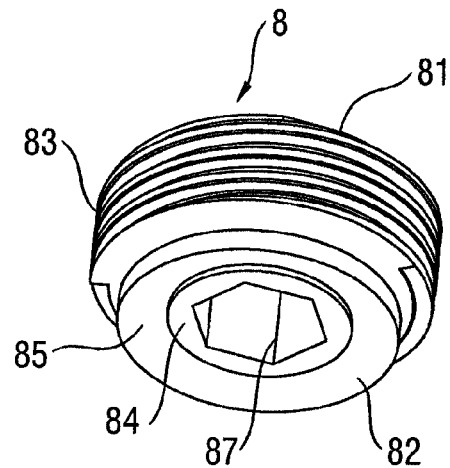
FIG. 6 shows a perspective view from the bottom of the locking member of the polyaxial bone anchoring device according to the first embodiment.
Figure 7:
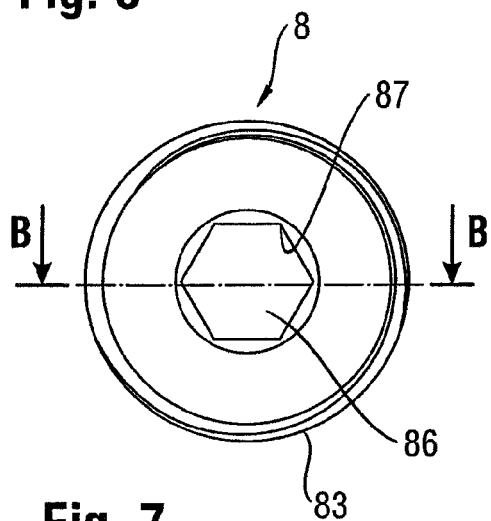
FIG. 7 shows a top view of the locking member shown in FIG. 6.
Figure 8:
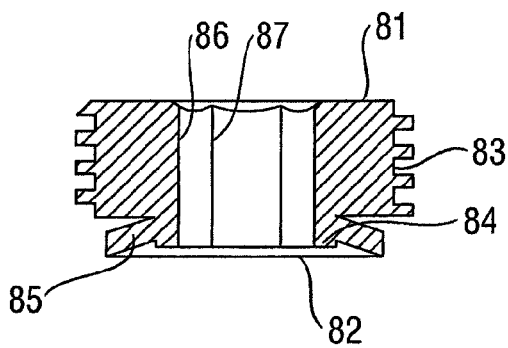
FIG. 8 shows a cross-sectional view of the locking member along line B-B in FIG. 7.

With reference to FIGS. 3 to 5, a pressure member 7 is of substantially cylindrical construction with an outer diameter sized so as to allow the pressure member 7 to be introduced into the second portion 53b of the bore of the receiving part 5 and to be moved therein in the axial direction. The pressure member 7 has a top end 71 and an opposite bottom end 72 and a longitudinal axis C extending through the two ends. The longitudinal axis C, in a mounted state, is the same as the longitudinal axis C of the receiving part 5. The pressure element 7 is arranged in the receiving part 5 such that its top end 71 is oriented towards the top end 51 of the receiving part and the bottom end 72 is oriented towards the bottom end 52 of the receiving part. At its top end 71, the pressure element 7 comprises a substantially U-shaped recess 73 that is configured to receive the rod 6. When the rod 6 is positioned on the bottom of the recess 73, the top end 71 of the pressure member 7 is located at a height above the surface of the rod 6.

At the top end 71, the pressure member comprises a collar 77 shaped as two opposite segments of a circle. Two enlarged surface portions 71a are formed at the upper end of the sidewalls of the U-shaped recess 73. The outer diameter of the pressure element 7 in the region of the collar 77 is enlarged so that the enlarged surface portions 71a extend into the first part 53a of the bore. The enlarged surface portions 71a provide an abutment for the locking member described below.

On its lower side, the pressure member 7 comprises a spherically-shaped recess 74 that cooperates with a spherical outer surface portion of the head 3. Furthermore, a coaxial through-hole 75 is provided in the pressure member 7 that allows access to a recess 4 of the head 3 when the bone anchoring element 1 and the pressure member 7 are mounted in the receiving part 5.

With reference to FIGS. 1 and 6 to 8, a locking member 8 in the first embodiment is a monolithic piece. It is formed as a set screw having a top end 81 and a bottom end 82 that faces the pressure member 7 when the locking member 8 is inserted between the legs 57, 58 of the receiving part 5. More in detail, the locking member 8 has adjacent to the top end 81 a screw portion 83 with an external thread that cooperates with the internal thread 59 of the legs 57, 58. On the bottom side of the screw portion 83 there is a cylindrical projection 84 surrounded by a conically outwardly extending portion 85 that is inclined away from the screw portion 83. The outer diameter of the conical portion 85 is smaller than the outer diameter of the screw portion 83 such that the locking member 8 can be inserted between the legs 57, 58 with its bottom end 82 first.

The cylindrical portion 84 is configured to be a rigid portion, i.e. it does not deform under normal operating conditions when it is pressed against the rod, which is described below. The conical portion 85 has a shape similar to a conical washer. It is configured to deform towards the screw portion 83, when it is pressed against the pressure member 7 described below. In particular, the conical portion 85 is elastically deformable so that it is resilient and returns to its original shape when the load is removed. Further, in the original configuration, the conical portion 85 protrudes from the cylindrical portion 84 in the axial direction. The conical portion 85 has a size and elasticity such that when a load is applied to it in the direction of the top end 81, the conical portion 85 is bent against the screw portion 83. In the bent configuration, the cylindrical portion 84 protrudes in an axial direction beyond the conical portion 85.

The locking member 8 further comprises a coaxial through-hole 86 with an engagement portion 87. The engagement portion 87 is a hexagonal recess. However, it can have any other shape such as a torx-shape or longitudinal grooves or any structure that allows engagement with a tool. The engagement portion 87 needs not to be provided on a through hole. It can also be provided as a recess with a depth extending into the locking member 8 from the top end.

The parts of the bone anchoring device are made of a bio-compatible material, for example, of a bio-compatible metal or a metal alloy, such as titanium, stainless steel, nickel titanium alloys, such as Nitinol, or made of a bio-compatible plastic material, such as PEEK (polyetheretherketone). The parts can be made all of the same or of different materials.

In use, the receiving part 5 and the anchoring element 1 as well as the pressure member 7 are usually pre-assembled such that the head 3 is pivotably held in the seat 55 of the receiving part 5 and the pressure member 7 is placed onto the head 3. At least two polyaxial bone anchoring devices shall be connected via a rod 6. After insertion of the bone anchoring elements into the bone, the receiving parts are aligned and the rod 6 is inserted.

The locking procedure will be explained with reference to FIGS. 9 to 13. First, as shown in FIG. 9, the locking member 8 is inserted into the receiving part 5 with the bottom end 82 of the locking member facing towards the rod 6. The locking member 8 is then further screwed-in until an outermost edge of the conical portion 85 contacts the top end surface 71a of the pressure member 7 that serves as an abutment. In this position, shown in FIG. 10, the conical portion 85 and the cylindrical portion 84 do not contact the rod 6. Therefore, the rod 6 is freely movable in the U-shaped recess 73 of the pressure member 7 that is aligned with the U-shaped recess 56 of the receiving part 5. When the conical portion 85 contacts the pressure member 7, pressure is exerted onto the head 3 via the pressure member 7. This clamps the head 3 in an adjustable angular position with respect to the receiving part 5 and holds the head 3 in this position by means of friction. The clamping force may be precisely adjusted to be higher or lower depending on how far the locking member 8 is screwed-in.

Further advancement of the locking member 8 towards the rod 6 leads to a deformation of the conical portion 85. The conical portion 85 is bent towards the screw portion 83 with the top end surface 71a of the pressure member 7 acting as an abutment (see FIG. 11).

Still further advancement of the locking member 8 towards the rod 6 increases the deformation of the conical portion 85 until the cylindrical portion 84 comes in contact with the surface of the rod 6 as shown in FIG. 12. By means of this, the head 3 and the rod 6 are locked.

It is possible to correct the position of the rod 6 without loosening of the locking of the head 3. To achieve this, the locking member 8 is screwed-back until the rod becomes movable. This is possible due to the resilient property of the conical portion 85. It may be even possible to fully remove the locking member 8 and to completely revise the positioning of the polyaxial bone anchoring device.

Figure 14:
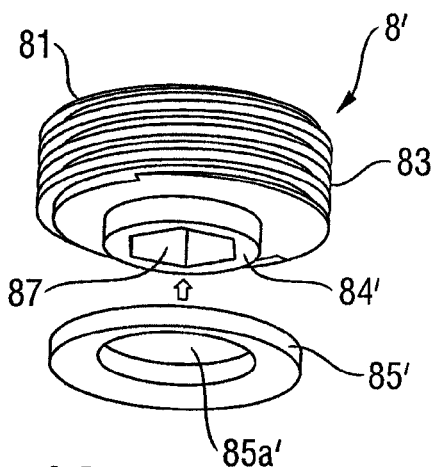
FIG. 14 shows a perspective exploded view of the locking member of the polyaxial bone anchoring device according to a second embodiment.
Figure 15:
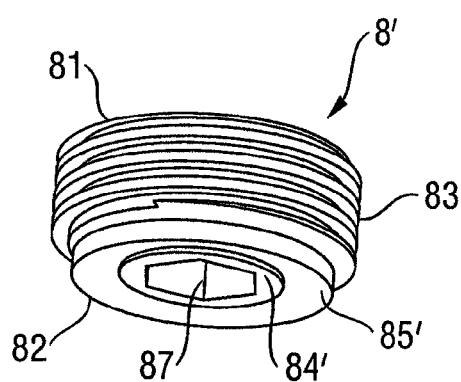
FIG. 15 shows a perspective view of the locking member of FIG. 14 in an assembled state.

A second embodiment of the polyaxial anchoring device will be described with reference to FIGS. 14 to 18. The second embodiment differs from the first embodiment in the design of the locking member. The locking member 8' according to the second embodiment comprises a conical portion 85' that is a separate member. The conical portion 85' has a shape similar to a conical washer, i.e. it has a coaxial hole 85a', the inner diameter of which is dimensioned such that the conical portion 85' can be placed around the cylindrical portion 84'. As shown in FIG. 14, the conical portion 85' is mounted from the side of the cylindrical portion 84' onto the locking member 8'. It can be press-fit onto the cylindrical portion 84' or crimped, welded or fixed with any other method. In the assembled state as shown in FIG. 15, the conical portion 85' is fixed to the screw portion 83 so that the locking member 8' forms a single part.

The conical portion 85' can be made of a different material compared to the material of the screw portion 83. Various conical portions 85' can be provided that differ with respect to the material, the cone angle, the thickness, or any other properties to allow for an adjustment of the clamping force by selecting an appropriate portion.

Figure 16:
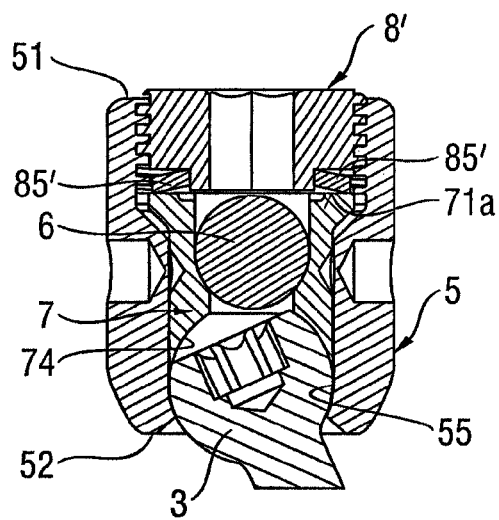
FIGS. 16 to 17 show cross-sectional views of steps of use of the polyaxial bone anchoring device according to the second embodiment, the section being taken in a plane perpendicular to the rod axis.
Figure 17:
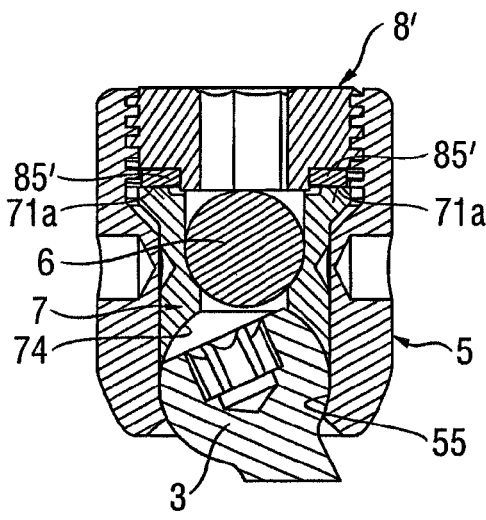
Figure 18:
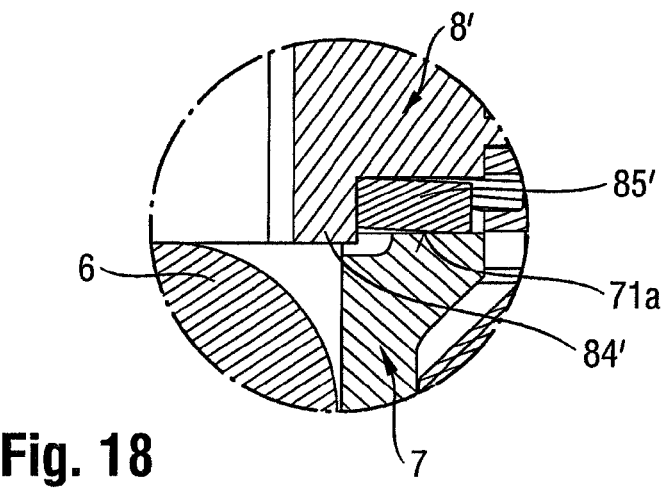
FIG. 18 shows an enlarged portion of a detail of FIG. 17.

In use, as shown in FIGS. 16 to 18, because the conical portion 85' projects from the cylindrical portion 84', the conical portion 85' comes first into contact with the top end surface 71a of the pressure member 7 and begins to clamp the head 3. Upon further insertion of the locking member 8', the conical portion 85' is deformed and the clamping force onto the head 3 is increased until the head 3 is locked. When the conical portion 85' has been deformed such that the cylindrical portion 84' protrudes, the cylindrical portion 84' comes into contact with the rod 6 and clamps the rod 6. Final tightening locks the whole assembly.

Various modifications of the previous embodiments are conceivable. In particular, the deformable portion doesn't have to be a conical ring-shaped portion. It is sufficient that a deformable portion is located at a position that comes into contact with the top end surface 71a of the pressure member. The ring-shaped portion is, however, particularly appropriate for a locking member that is advanced by screwing it between the legs.

For the polyaxial bone anchoring device, any known polyaxial bone anchoring devices can be used that comprise a bone anchoring element that is pivotably received in a receiving part. In particular, bone anchoring devices, wherein the bone anchoring element is introduced from the bottom end of the receiving part into the receiving part may be used. The design of the receiving part can be different. As for the bone anchoring element, any known bone anchors, such as screws, nails, with or without canulation, can be used.

The connection between the locking member and the receiving part does not necessarily have to be a threaded connection. Other connections may be possible, such as, for example, a bayonet connection.

The invention claimed is:

1. A polyaxial bone anchoring device comprising:
   a bone anchoring element having a shank configured to be anchored to a bone and a head;
   a receiving part configured to be coupled to the shank and to pivotably receive the head, the receiving part having a longitudinal axis and a channel for receiving a rod;
   a pressure member configured to be received in the receiving part and to exert pressure onto the head to lock the head in the receiving part;
   a locking member that is insertable into the channel, the locking member comprising a top end, a bottom end configured to face the pressure member, a deformable first portion provided at the bottom end, and a second portion provided at the bottom end;
   wherein when the head of the bone anchoring element, the pressure member and the rod are in the receiving part and the locking member is advanced into the channel along the longitudinal axis, the locking member is moveable between a first position wherein the deformable first portion is deformed axially towards the top end of the locking member while a load is applied by the deformable first portion to the pressure member such that the pressure member clamps the head in an angular position that remains adjustable, and a second position further into the channel wherein the deformable first portion is deformed further axially towards the top end of the locking member and wherein the second portion is in contact with the rod and clamps the rod.

2. The polyaxial bone anchoring device of claim 1, wherein the deformable first portion is elastically deformable.

3. The polyaxial bone anchoring device of claim 1, wherein the second portion is a rigid portion.

4. The polyaxial bone anchoring device of claim 1, wherein the second portion is provided closer to the longitudinal axis than the deformable first portion.

5. The polyaxial bone anchoring device of claim 1, wherein when the locking member is in the first position, the deformable first portion projects farther outward in an axial direction than the second portion.

6. The polyaxial bone anchoring device of claim 1, wherein the deformable first portion and the second portion are a monolithic section of the locking member.

7. The polyaxial bone anchoring device of claim 1, wherein the deformable first portion and the second portion are separate parts that are connected together.

8. The polyaxial bone anchoring device of claim 1, wherein the deformable first portion is ring-shaped.

9. The polyaxial bone anchoring device of claim 1, wherein the deformable first portion is inclined with an angle of inclination that opens towards the pressure member.

10. The polyaxial bone anchoring device of claim 1, wherein the pressure member comprises a channel to receive the rod and wherein sidewalls of the channel extend above the surface of the rod when the rod is seated in the channel.

11. The polyaxial bone anchoring device of claim 1, wherein the pressure member is a substantially cylindrical part with a top end and a bottom end and a U-shaped recess at the top end for receiving the rod, and two open legs.

12. The polyaxial bone anchoring device of claim 1, wherein an end surface of the pressure member that comes into contact with the deformable first portion has such a size that it forms an abutment for the deformable first portion over at least a portion of the length along which the deformable first portion is deformed.

13. The polyaxial bone anchoring device of claim 1, wherein the receiving part comprises a top end, a bottom end, and a bore extending from the top end to the bottom end, and wherein the channel for the rod is formed by a recess adjacent the top end with a substantially U-shaped cross-section.

14. The polyaxial bone anchoring device 10 claim 13, wherein by the recess two open legs are formed and wherein an internal thread is provided on the legs that cooperates with an external thread on the locking member.

15. The polyaxial bone anchoring device of claim 1, wherein the locking member is a set screw.

16. The polyaxial bone anchoring device of claim 1, wherein at the second end of the locking member, the second portion of the locking member is exposed to the outside of the locking member at a central region of the first portion.

17. The polyaxial bone anchoring device of claim 16, wherein in the first position, at least some of the first portion is closer to the head than the second portion is to the head, and wherein in the second position, the second portion is closer to the head than the entire first portion is to the head.

18. The polyaxial bone anchoring device of claim 1, wherein a gap separates the deformable first portion from other portions of the locking member in a direction of the longitudinal axis, and wherein the gap is sized such that when in the second position, at least some of the first portion is configured to be bent against the other portions of the locking member.

19. A polyaxial bone anchoring device comprising:
a bone anchoring element having a shank configured to be anchored to a bone and a head;
a receiving part configured to be coupled to the shank and to pivotably receive the head, the receiving part having a longitudinal axis and a channel for receiving a rod;
a pressure member configured to be received in the receiving part and to exert pressure onto the head to lock the head in the receiving part;
a locking member that is insertable into the channel, the locking member comprising a top end, a bottom end configured to face the pressure member, an external locking structure configured to cooperate with a corresponding internal locking structure of the receiving part, and a deformable first portion and a second portion provided at the bottom end, wherein the deformable first portion is connected to a rigid portion of the locking member at a position that is closer radially to the external locking structure than it is to a central axis of the locking member; and
wherein when the head of the bone anchoring element, the pressure member and the rod are in the receiving part and the locking member is advanced into the channel along the longitudinal axis, the locking member is moveable between a first position wherein the deformable first portion is in contact with the pressure member and a second position further into the channel wherein the deformable first portion is deformed and the second portion is in contact with the rod.

20. A polyaxial bone anchoring device comprising:
a bone anchoring element having a shank configured to be anchored to a bone and a head;
a receiving part configured to be coupled to the shank and to pivotably receive the head, the receiving part having a longitudinal axis and a channel for receiving a rod;
a pressure member configured to be received in the receiving part and to exert pressure onto the head to lock the head in the receiving part;
a locking member that is insertable into the channel, the locking member comprising a top end, a bottom end configured to face the pressure member, a bore extending from the top end along a central axis of the locking member for engaging a tool, and a deformable first portion and a second portion provided at the bottom end, wherein the deformable first portion is connected to a rigid portion of the locking member at a position that is farther radially from the central axis than an inner wall of the locking member defining the bore; and
wherein when the head of the bone anchoring element, the pressure member and the rod are in the receiving part and the locking member is advanced into the channel along the longitudinal axis, the locking member is moveable between a first position wherein the deformable first portion is in contact with the pressure member and a second position further into the channel wherein the deformable first portion is deformed and the second portion is in contact with the rod.

21. A polyaxial bone anchoring device comprising:
a bone anchoring element having a shank configured to be anchored to a bone and a head;
a receiving part configured to be coupled to the shank and to pivotably receive the head, the receiving part having a longitudinal axis and a channel for receiving a rod;
a pressure member configured to be received in the receiving part and to exert pressure onto the head to lock the head in the receiving part;
a locking member that is insertable into the channel, the locking member comprising a top end, a bottom end configured to face the pressure member, a deformable first portion provided at the bottom end, and a second portion provided at the bottom end;
wherein when the head of the bone anchoring element, the pressure member and the rod are in the receiving part and the locking member is advanced into the channel along the longitudinal axis, the locking member is moveable from a first position wherein the deformable first portion is deformed axially towards the top end of the locking member while a load is applied by the deformable first portion to the pressure member such that the pressure member clamps the head in an angular position that remains adjustable, to a second position further into the channel than the first position wherein the deformable first portion is deformed axially towards the top end of the locking member by more than the axial deformation at the first position and wherein the head is locked, and to a third position further into the channel than the second position wherein the deformable first portion is deformed axially towards the top end of the locking member by more than the axial deformation at the second position and wherein the second portion is in contact with the rod and clamps the rod.

* * * * *

UNITED STATES PATENT AND TRADEMARK OFFICE
CERTIFICATE OF CORRECTION

| | | |
|---|---|---|
| PATENT NO. | : 9,510,868 B2 | Page 1 of 1 |
| APPLICATION NO. | : 13/907329 | |
| DATED | : December 6, 2016 | |
| INVENTOR(S) | : Lutz Biedermann et al. | |

It is certified that error appears in the above-identified patent and that said Letters Patent is hereby corrected as shown below:

In the Claims

Column 7, Line 32, Claim 14       Delete "10 claim 13",
Insert --of claim 13--

Signed and Sealed this
Eighth Day of August, 2017

Joseph Matal
*Performing the Functions and Duties of the*
*Under Secretary of Commerce for Intellectual Property and*
*Director of the United States Patent and Trademark Office*